US00PP20935P2

(12) United States Plant Patent
Egger

(10) Patent No.: US PP20,935 P2
(45) Date of Patent: Apr. 13, 2010

(54) ***HEUCHERA* PLANT NAMED 'PLUM ROYALE'**

(50) Latin Name: ***Heuchera* hybrid**
Varietal Denomination: Plum Royale

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/321,467

(22) Filed: Jan. 20, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner*—Kent L Bell
(74) *Attorney, Agent, or Firm*—Klarquist Sparkman, LLP

(57) ABSTRACT

A new and distinct hybrid of *Heuchera* plant characterized by shiny plum purple colored leaves in spring and summer, older leaves with strongly veiled foliage tinted red purple which gives the plant a silvered look, pink-white flowers on dark peduncles, excellent vigor, and a mounding, compact habit.

1 Drawing Sheet

Botanical denomination: *Heuchera* hybrid.
Variety designation: 'Plum Royale'.

BACKGROUND OF THE INVENTION

The present invention relates to a new and distinct cultivar of *Heuchera* hybrid and given the cultivar name of 'Plum Royale'. *Heuchera* is in the family Saxifragaceae. *Heuchera* 'Plum Royale' originated from a cross between *Heuchera* 637-2, a proprietary non-commercial hybrid, as the seed parent, and *Heuchera* 647-8, a proprietary non-commercial hybrid, as, as the pollen parent.

Compared to the seed parent, *Heuchera* 637-2, the new hybrid is much more vigorous, has flowers that are pink and white rather than green fading red. Compared to the pollen parent, *Heuchera* 647-8, the new hybrid has shiny plum purple colored leaves rather than dull rose colored leaves.

This new *Heuchera* is distinguished by:

1. Shiny plum purple colored leaves year in late spring, summer, and fall,
2. older and winter leaves with strongly veiled foliage tinted red purple which gives the plant a silvered look,
3. pink-white flowers on dark peduncles,
4. excellent vigor, and
5. a mounding, compact habit.

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a one-and-a-half year-old plant of *Heuchera* 'Plum Royale' in spring growing in the ground in full sun in the trial field in August in Canby, Oreg.

FIG. 2 shows the same plant in flower in August.

DETAILED PLANT DESCRIPTION

The following is a detailed description of the new *Heuchera* cultivar based on observations taken in August of a one-year-old specimen growing in the ground in the trial bed under high shade and with added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—19 cm tall from top of the foliage to the ground and 37 cm wide.
*Habit.*—Mounding.
*Vigor.*—Excellent.
*Roots.*—Fibrous, freely branching, fine, and white in color; roots develop easily from tip cuttings.

Leaf:

*Type.*—Simple.
*Arrangement.*—Rosette.
*Shape.*—Broadly ovate.
*Lobing/division.*—7 shallow lobes, the terminal is the longest.
*Venation.*—Palmate.
*Margins.*—Broadly crenate and somewhat undulate.
*Apex.*—Obtuse.
*Base.*—Cordate, lobes overlapping at the base.
*Blade size.*—9.5 cm to 14.5 cm long and 8.5 cm to 11.5 cm wide.
*Surface texture.*—Glandular on both sides, mostly short.
*Appearance.*—Very glossy on younger leaves, older leaves not glossy.
*Petiole description.*—9.5 cm to 14 cm long and 2 mm wide, glandular hairs, Greyed Orange 177A to Grey Brown 199A.
*Leaf color.*—Topside, new mature leaves are between Red Purple 71A and Greyed Purple 187A with Black 202A veins; slightly older mature leaves start to get a silver cast interveinally; oldest mature leaves are closest to pewter (Black 202B) with red purple tints (between Red Purple 71A and Greyed Purple 187A) and veins closest to Brown 200A; bottom side color of all stages between Greyed Purple 187A and Greyed Purple 187B.

Inflorescence:

*Size.*—4 cm wide and 24 cm long.

*Type.*—Thyrse.

*Number of flowers per thyrse.*—About 100.

*Number of thyrse.*—5.

*Peduncle.*—Grows to 48 cm tall, 3 mm wide at base, Greyed Purple 187A, glandular hairs, with 0 to 2 petiolate cauline leaves (broadly ovate, blades to 4 cm long and 4 cm wide with a lobed and incised margin, between Red Purple 71A and Greyed Purple 187A with veins Black 202A).

*Pedicel.*—Variable in size, with glandular hairs, Greyed Purple 187A.

*Bloom period.*—Late June through July in Canby, Oreg.

Flower bud:

*Size.*—2.7 mm wide and 4 mm long.

*Description.*—Glandular puberulent, ovoid.

*Color.*—Greyed Purple 186A with White 155D in 5 bands where calyx lobes meet.

Flower:

*Type.*—Perfect.

*Shape.*—Campanulate.

*Size.*—6 mm long and 5 mm wide.

*Petal description.*—5 in number, 3 mm long and 1.8 mm wide, spatulate, tip acute, margin entire, glabrous and Red Purple 65D on both sides.

*Calyx description.*—Campanulate, 6 mm long and 5 mm wide, with 5 lobes divided ⅔ way to the base, each 1.5 mm wide and 2.5 mm long, glandular hairs outside and glabrous inside, tips obtuse, margin entire; outside Red Purple 61A in the middle of each lobe and edges and base Red Purple 65C to 65D; inside Red Purple 65C with center darker Red Purple 61A; before drying to brown the calyx is Yellow 146B.

*Stamen description.*—5 in number, filaments 3 mm long, White 155D, anthers sterile, 0.5 mm, Yellow White 158A.

*Pistil description.*—1, 2-beaked, 4 mm long, Yellow Green 154D overall, ovary 1 mm long, style 3 mm long, both Yellow White 158A, stigma Red Purple 60D.

*Fragrance.*—None.

*Lastingness.*—Each thyrse blooms for about 2 weeks on the plant.

Fruit:

*Type.*—Two beaked capsule.

*Size.*—7 mm deep by 4 mm wide.

*Fertility.*—Good.

*Color.*—Brown 200D.

Seed:

*Shape.*—Linear.

*Size.*—1 mm long.

*Color.*—Black, RHS 202A.

Pest and disease tolerance: Excellent disease resistance to powdery mildew, the common problem of *Heuchera*. Susceptible to *Heuchera* rust and root weevils.

COMPARISON TO SIMILAR *HEUCHERA*

Compared to *Heuchera* 'Plum Pudding' (an unpatented plant) the new hybrid has leaves that hold strong red purple color in the summer and hold tints of red purple in fall and winter. The new hybrid has very dark veins.

I claim:

1. A new and distinct *Heuchera* plant as herein illustrated and described.

* * * * *

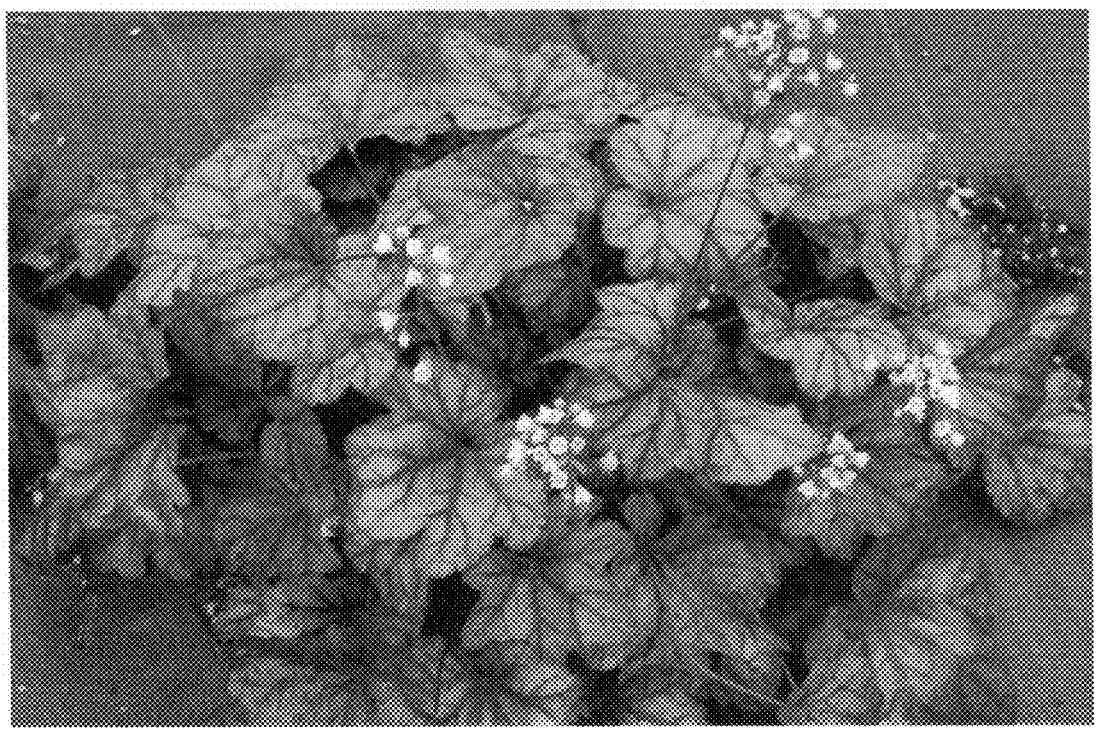

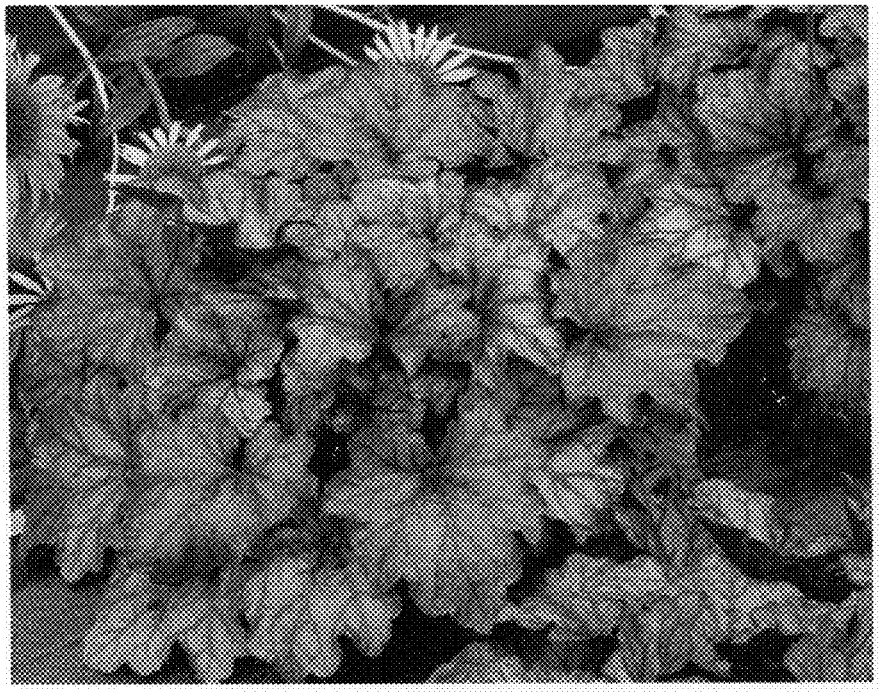
FIG. 1: left
FIG 2: below